United States Patent
Wenk et al.

(10) Patent No.: US 8,703,159 B2
(45) Date of Patent: *Apr. 22, 2014

(54) COSMETIC COMPOSITION CONTAINING POLYGLYCEROL PARTIAL ESTER

(75) Inventors: Hans Henning Wenk, Muelheim an der Ruhr (DE); Peter Lersch, Dinslaken (DE)

(73) Assignee: Evonik Goldschmidt GmbH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/578,105

(22) PCT Filed: Jan. 12, 2011

(86) PCT No.: PCT/EP2011/050304
§ 371 (c)(1),
(2), (4) Date: Aug. 9, 2012

(87) PCT Pub. No.: WO2011/098311
PCT Pub. Date: Aug. 18, 2011

(65) Prior Publication Data
US 2012/0309996 A1    Dec. 6, 2012

(30) Foreign Application Priority Data
Feb. 12, 2010    (EP) ..................................... 10153429

(51) Int. Cl.
*A61K 9/00*    (2006.01)
*C07C 59/01*    (2006.01)

(52) U.S. Cl.
USPC .......................................... 424/400; 554/213

(58) Field of Classification Search
None
See application file for complete search history.

(56) References Cited

U.S. PATENT DOCUMENTS

| | | | |
|---|---|---|---|
| 3,936,391 A | 2/1976 | Gabby et al. | |
| 4,046,874 A | 9/1977 | Gabby et al. | |
| 4,736,756 A | 4/1988 | Grollier | |
| 5,024,787 A | 6/1991 | Jakobson et al. | |
| 5,147,644 A | 9/1992 | Oppenlaender et al. | |
| 5,424,469 A * | 6/1995 | Jakobson et al. | 554/227 |
| 5,711,942 A * | 1/1998 | Eicken et al. | 424/70.1 |
| 2007/0196400 A1 | 8/2007 | Raschke et al. | |
| 2011/0091399 A1 | 4/2011 | Meyer et al. | |
| 2011/0201538 A1 | 8/2011 | Wenk et al. | |
| 2011/0300082 A1 | 12/2011 | Wenk et al. | |

FOREIGN PATENT DOCUMENTS

| | | |
|---|---|---|
| DE | 3533600 A1 | 4/1986 |
| DE | 3818292 A1 | 12/1989 |
| DE | 102008001788 A1 | 11/2009 |
| EP | 0451461 B1 | 10/1991 |
| EP | 0780117 A1 | 6/1997 |
| EP | 1 488 775 A1 | 12/2004 |
| EP | 1 623 694 A1 | 2/2006 |
| EP | 1 704 846 A1 | 9/2006 |
| JP | 2008195689 | 8/2008 |
| JP | 2008208050 | 9/2008 |
| JP | 2008280329 | 11/2008 |
| JP | 2008308415 | 12/2008 |
| WO | WO 2004/009047 A1 | 1/2004 |
| WO | WO2005115328 | 12/2005 |
| WO | WO 2008/012220 A1 | 1/2008 |

OTHER PUBLICATIONS

Polydispersity Index, Wikipedia, the free encyclopedia, May 10, 2010, Retrieved from the Internet: URL:http://en.wikipedia.org/wiki/Polydispersity_index.
International Search Report dated May 17, 2011 issued in PCT/EP2011/050304.
Mashiko, T. et al., "Application of polyglycerin diisostearate to hair care products", Fragrance Journal, 1998, pp. 64-70, 26(5).
Cassel, S., et al., "Original Synthesis of Linear, Branched and Cyclic Oligoglycerol Standards", European Journal of Organic Chemistry, Mar. 2001, pp. 875-896, vol. 2001, Issue 5.

* cited by examiner

*Primary Examiner* — Robert A Wax
*Assistant Examiner* — William Craigo
(74) *Attorney, Agent, or Firm* — Scully, Scott, Murphy & Presser, P.C.

(57) ABSTRACT

The present invention relates to cosmetic compositions containing polyglycerol partial esters of linear, unsubstituted carboxylic acids and bifunctional carboxylic acids with the provisos that the polyglycerol partial ester comprises an HLB-value from 2 to 10 and that the polyglycerol obtained by hydrolysis or alcoholysis of the polyglycerol partial ester comprises an average degree of polymerization of from 2 to 8 and at least 1% of the polyglycerol comprises cyclic structures. The present invention also relates to the use of aforementioned polyglycerol esters for the production of and use in cosmetic compositions.

8 Claims, No Drawings

COSMETIC COMPOSITION CONTAINING POLYGLYCEROL PARTIAL ESTER

FIELD OF THE INVENTION

The present invention relates to cosmetic compositions containing polyglycerol partial esters of linear, unsubstituted carboxylic acids and bifunctional carboxylic acids with the provisos that the polyglycerol partial ester comprises an HLB-value from 2 to 10 and that the polyglycerol obtained by hydrolysis or alcoholysis of the polyglycerol partial ester comprises an average degree of polymerization of from 2 to 8 and at least 1% of the polyglycerol comprises cyclic structures. The present invention also relates to the use of aforementioned polyglycerol esters for the production of and use in cosmetic compositions.

BACKGROUND OF THE INVENTION

The use of polyglycerol esters in cosmetic applications is known per se:

German Patent Publication DE 38 18 292 A1 relates to a process for the preparation of fatty acid or hydroxy fatty acid esters of isopropylidene derivatives of a polyglycerol and their use for cosmetic preparations and skin care agents.

European Publication EP 0 451 461 B1 describes the use of mixtures of polyglycerol fatty acid esters as emulsifiers in cosmetic and pharmaceutical preparations. These are obtainable by partial esterification of polyglycerols with at least one saturated fatty acid having 12 to 22 C atoms or at least one unsaturated fatty acid having 16 to 22 C atoms, where the unsaturated fatty acid or fatty acid mixture employed can additionally contain up to 10% by weight of saturated fatty acids having 16 to 22 C atoms. The degree of esterification of the saturated or unsaturated fatty acids in the mixture is between 20 and 70%.

JP2008308415 describes hair rinses, hair treatments, or hair conditioners which suppress increased volume of hair in high moisture environments and contain methacrylate polymers, fatty acid polyglycerin esters, alditols, and cationic surfactants. Diglycerol diisostearate is given as a suitable example of a polyglycerol ester.

JP2008280329 describes polyglycerin fatty acid esters as gelling agents for cosmetic oils.

JP2008208050 describes detergents containing polyalkyl glucoside derivatives and polyglycerin monofatty acid esters (monoesterification degree >=70%) having excellent foaming properties and good skin compatibility.

JP2008195689 describes skin and hair care compositions comprising microemulsions and containing polyglycerin esters with C8-22 fatty acids and having an HLB value >=13.

WO2005115328 discloses skin and hair care products having an improved performance profile containing cationic polymers and polyglycerin fatty acid esters.

Mashiko et al. describe the use of polyglycerin isostearates in hair care products (Fragrance Journal 1998, 26(5), 64-70).

Takano et al. describe the use of Nikkomulese 61H (containing polyglyceryl-10 pentastarate) for hair conditioner applications.

EP780117 discloses hair conditioning emulsions containing a C6-22 fatty acid ester with polyglycerol.

DE3533600 discloses hair preparations containing water soluble, polyglycerol containing non-ionic surfactants.

It was an object of the invention to provide agents which overcome at least one disadvantage listed in the prior art.

It has now been found, surprisingly, that cosmetic compositions containing polyglycerol partial esters of claim 1 fulfill the requirements.

The present invention therefore relates to cosmetic compositions containing polyglycerol partial ester having the structure of Formula (I)

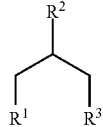

Formula (I)

with $R^1$, $R^2$ and $R^3$ independent from each other, equal or different selected from the group consisting of
- —OH,
- —$OR^4$, with $R^4$ a linear, unsubstituted acyl radical with a chain length of from 16 to 22 carbon atoms with the proviso that the monocarboxylic acids obtained from the acyl radical by saponification bears an iodine value of smaller than 50, preferred smaller than 30, more preferred about 1-25,
- —$OR^5$, with $R^5$ a radical having the structure of Formula (I) wherein one of $R^1$, $R^2$ and $R^3$ being a direct bond to the oxygen of —$OR^5$ wherein each molecule of the polyglycerol partial ester comprises at least one of each —$OR^4$ and —$OR^5$,
with the provisos that the polyglycerol obtained by hydrolysis or alcoholysis of the polyglycerol partial ester comprises an average degree of polymerization of from 2 to 8 and the polydispersity index of said polyglycerol is greater than 0.75, preferably greater than 1.0, particularly preferred greater than 1.2, as specified below.

The invention further relates to the use of the polyglycerol partial esters in cosmetic preparations.

An advantage of the present invention is that the cosmetic preparations according to the invention are long time storage stable.

A further advantage of the present invention is that the cosmetic preparations comprising the polyglycerol partial esters are stable at high temperature and also withstand repeated freeze-thaw-cycles.

Yet a further advantage is that the cosmetic preparations according to the invention might give a light, non-greasy skin feel.

Yet a further advantage of the present invention is that the cosmetic preparations might enhance the combability of hair.

Yet a further advantage of the present invention is that the cosmetic preparations might enhance the grip of hair.

Yet a further advantage of the present invention is that the cosmetic preparations might enhance the look of hair.

Yet a further advantage of the present invention is that the cosmetic preparations might enhance the elasticity of hair.

Yet a further advantage of the present invention is that the cosmetic preparations may protect human or animal hair against heat damage.

Still another advantage of the present invention is that the polyglycerol partial esters may need little deposition aid to settle on fibers.

Yet a further advantage of the present invention is that the cosmetic preparations according to the invention may have an enhanced deposition of the polyglycerol partial ester in the presence of an anionic surfactant.

Another advantage is that the cosmetic compositions according to the invention may provide excellent static control on fibers.

A further advantage is that the polyglycerol partial esters used in the invention may have excellent emulsifying properties.

Another advantage is that the cosmetic compositions according to the invention may be biodegradable and may have a low human and environmental toxicity.

Yet another advantage is that the cosmetic compositions according to the invention may allow for formulation with material that are not stable at low pH such as enzymes and certain perfumes.

The person skilled in the art will acknowledge that polyglycerol esters due to their polymeric nature and due to the methods they are prepared by are statistical mixtures of different structures.

Thus, a polyglycerol molecule may comprise ether bonds between two primary positions, a primary and a secondary position, or two secondary positions of the glycerol monomer units. Cyclic structures comprising one or more cycles may also be present. For tetraglycerol and higher oligomers, branched structures comprising at least one glycerol monomer unit linked to three further glycerol monomer units via an ether linkage may be present. A polyglycerol mixture may contain different oligomers and isomers of these, and may be characterized by the oligomer distribution, i. e. the proportion of mono-, di-, tri-, . . . -glycerol structures in the mixture. This distribution can for example be determined by high temperature gas chromatography of the polyglycerol mixture after derivatization. Synthesis of single oligoglycerol isomers is described in "Original synthesis of linear, branched and cyclic oligoglycerol standards", Cassel et al., Eur. J. Org. Chem. 2001, 875-896.

Additionally, the esterification of polyglycerol mixtures typically results in a distribution of non-esterified polyglycerol, monoester, diester, triester, etc., where the average degree of esterification is determined by the ratio of fatty acid (or its derivative) to polyglycerol used in the synthesis. If a mixture of different fatty acids is used for the esterification, more than one equal or different fatty acid residues may be linked to one polyglycerol molecule via ester linkage.

For the present invention it is essential that the polyglycerol backbone of the polyglycerol partial ester comprises an average degree of polymerization of from 2 to 8, preferred from 2.5-6, particularly preferred from about 3 to 5.

A suitable method for determining the mean degree of polymerization of the polyglycerol in a given polyglycerol partial ester comprises hydrolysis or alcoholysis of the partial ester, separation of the resulting polyglycerol from the formed carboxylic acid compounds, and analysis by gas chromatography (GC) after derivatization. The GC method also allows differentiating cyclic from non-cyclic structures for oligomers with up to four monomer units (i. e. glycerol to tetraglycerols).

For the calculation of the polydispersity index described below, cyclic and linear structures are added, e. g. the proportion of diglycerol in a mixture consists of the proportion of linear and cyclic diglycerol structures. For this purpose, the 0.6 g polyglycerol ester is refluxed in 25 ml of 0.5 N ethanolic KOH for 30 minutes and adjusted to pH 2-3 with sulphuric acid. The fatty acids are separated by threefold extraction with an equivalent volume of petroleum ether. The combined extracts are evaporated to a volume of approx. 10 ml. A 0.5 ml aliquot is transferred to an autosampler vial and analyzed by GC after addition of 0.5 ml MTBE and 1 ml TMPAH solution (trimethylanilinium hydroxide in methanol) as derivatization agent.

Fatty acid GC-analysis is carried out with a gas-chromatograph equipped with split/splitless injector, capillary column and a flame ionisation detector.
Conditions:

| | |
|---|---|
| Injector | 290° C., Split 30 ml |
| Injection volume: | 1 μl |
| Column: | 30 m *0.32 mm HP1 0.25 μm |
| Carrier gas | helium, head pressure 70 kPa |
| Temp. prog. (conditioning) | 80° C.-300° C. with 8° C./min; |
| Detector: | FID at 320° C. |
| | hydrogen 35 ml/min |
| | air 240 ml/min |
| | make up gas 35 ml/min |

Applying these conditions the fatty acids methyl esters are separated according to their alkyl chain length.

The relative content of the individual fatty acids (chain length distribution) is evaluated by peak area percentage. The residue after extraction with petroleum ether is adjusted to pH 7-8 by addition of barium hydroxide solution. The precipitate of barium sulphate is separated by centrifugation. The supernatant is removed and the residue extracted thrice with 20 ml of ethanol. The combined supernatants are evaporated at 80° C./50 mbar. The residue is dissolved in pyridine. 500 μl of the solution are transferred to an autosampler vial and 1 ml of MSTFA (N-Methyl-N-trifluoroacetamide) is added. The vial is closed and heated to 80° C. for 30 minutes.

GC-analysis of the polyglycerol component (as its trimethylsilyl derivative) is carried out with a gas-liquid chromatograph equipped with a on column injector and FID detector.
Conditions:
Injector: on column, oven tray
Injection volume: 0.1 μl
Carrier gas: 3 ml/min Hydrogen (constant flow)
Column SimDist 12 m×0.32 mm×0.1 μm (Varian)
Temperature program: 65° C.-365° C., 10° C./min
Detector (FID): 375° C.

Under these conditions, polyglycerols are separated according to their degree of polymerization. Additionally, cyclic isomers are separated from linear ones up to a degree of polymerization of four.

The peak areas of the individual oligomers are separated by a perpendicular applied at the lowest point of the peak valley in between.

Since the resolution of oligomers higher than hexaglycerol is poor, peaks of heptaglycerol and higher oligomers are summarized as "heptaglycerol and higher" and treated as heptaglycerol for the purpose of polydispersity index calculation. Also, for the calculation of the polydispersity index linear and cyclic isomers are summarized.

The relative ratio of the individual polyglycerol oligomers and isomers is calculated from the peak area of the GC obtained as described.

Of course, the described GC analyses of the fatty acid component and polyglycerol component can also be performed on the raw materials which had been used for the preparation of the polyglycerol esters contained in the cosmetic compositions according to the invention.

For the present invention it is essential that polyglycerol obtained by hydrolysis or alcoholysis of the polyglycerol partial ester contained in the cosmetic compositions according to the invention comprises a polydispersity index of greater than 0.75, preferably greater than 1.0, more preferably greater than 1.5.

For the purpose of the present invention, the polydispersity index is calculated as $$\sum_i |n_i - \langle n \rangle| \cdot x_i,$$

where $n_i$ is the degree of polymerization of the single oligomer i, $\langle n \rangle$ is the average degree of polymerization of the polyglycerol mixture, and $x_i$ is the proportion of the oligomer i in the polyglycerol mixture as determined by the GC method described above. For this calculation, the average degree of polymerization $\langle n \rangle$ is calculated from the hydroxyl value (OHV, in mg KOH/g) according to the formula $\langle n \rangle = (112200-18*OHV)/(74*OHV-56100)$.

Polyglycerol depending on its way of preparation can comprise different percentages of cyclic structures. An overview of some cyclic structures present in commercial polyglycerol mixtures is given in "Original synthesis of linear, branched and cyclic oligoglycerol standards", Cassel et al., Eur. J. Org. Chem. 2001, 875-896. For the polyglycerol partial esters contained in the cosmetic compositions according to the present invention it is advantageous if the polyglycerol in the polyglycerol backbone of the partial ester comprises at least 1%, preferably at least 2% and even more preferred at least 3% cyclic structures.

The given percentages are neither percentages by weight nor per mole but are determined by the GC method described above and base on the amount of all polyglycerol.

The radicals $R^5$ in the polyglycerol partial ester might be the same or different within one molecule, preferably they are different.

It is obvious, that the residue —$OR^4$ is determined by the monocarboxylic acid $HOR^4$ used in the esterification reaction for preparing the polyglycerol partial ester. Preferred residues —$OR^4$ are accordingly derived from the acids selected from the group consisting of palmitic acid, stearic acid, arachidic acid, and behenic acid. Mixtures of different acids can be used, too, especially technical mixtures like for example fully or partially hydrogenated palm fatty acids, palm kernel fatty acids, coconut fatty acids, soybean fatty acids, tallow fatty acids, rapeseed fatty acids, high erucic rapeseed fatty acids or distilled fractions of these as long as their iodine value is smaller than 50, preferred smaller than 30 and more preferred smaller than 25. Depending on the degree of hydrogenation and the raw material, these technical mixtures can contain certain amounts of unsaturated fatty acids which then are contained in the polyglycerol partial ester contained in the cosmetic composition according to the invention. Typical examples of these unsaturated fatty acids are palmitoleic acid, oleic acid, elaidic acid, erucic acid, linoleic acid, and linolenic acid, where oleic acid and elaidic acid are most commonly found as constituents of partially hydrogenated fatty acid mixtures. The amount of this byproduct can be determined by the iodine value of the fatty acids obtained from the acyl radical by saponification of the polyglycerol partial ester. It is essential to the polyglycerol partial ester of the present invention, that this iodine value is smaller than 50, more preferred smaller than 30 and even more preferred from 1 to 25.

The iodine value can be determined by DIN 53241-1:1995-05.

Preferred polyglycerol partial esters contained in the cosmetic composition according to the present invention comprise a hydrophilic-lipophilic balance value (HLB value) of between 2 and 10, preferably of between 2.5 to 8, more preferably of between 3 to 6. The HLB value is a measure of the degree to which the molecule is hydrophilic or lipophilic, determined by calculating values for the different regions of the molecule. For the purpose of the present invention, the HLB value of the polyglycerol partial esters is calculated as follows:

$$HLB = (mp/(mp+ma))*20,$$

where mp is the mass of polyglycerol, and ma is the mass of carboxylic acid mixture used in the synthesis of the polyglycerol ester. For example, esterification of 100 g polyglycerol with 100 g fatty acids would result in an HLB of (100 g/(100 g+100 g))*20=10, independent of the degree of polymerization of the polyglycerol and the type of carboxylic acids used.

Preferred polyglycerol partial ester contained in the cosmetic composition according to the invention are characterized in that they have a melting point of at least 25° C., preferably of at least 35° C., more preferably of at least 38° C. and even more preferably of from 38° C. to 75° C.

The partial esters contained in the cosmetic composition according to the present invention are obtainable by a process of esterification of a) a polyglycerol mixture comprising an average degree of polymerization of from 2 to 8, preferred from 2.5-6, particularly preferred from about 3 to 5, and a polydispersity index of greater than 0.75, preferably greater than 1.0, more preferably greater than 1.5, with b) at least one monocarboxylic acid comprising a carboxylic acid $HOR^4$, with $R^4$ a linear, unsubstituted acyl radical with a chain length of from 16 to 22 carbon atoms with the proviso that the at least one carboxylic acid bears an iodine value of smaller than 50, preferred smaller than 30, more preferred about 1-25.

It may be beneficial to apply a catalyst (e. g. hydroxides or carbonates of alkali metals; hydroxides of alkaline earth metals; sulfonic acid catalysts like p-toluenesulfonic acid, methanesulfonic acid, trifluoromethanesulfonic acid; metal oxides like zinc(II)oxide or tin(II)oxide) in the esterification process, however the reaction may be performed without addition of a catalyst. The esterification reaction is typically performed at temperatures between 160 and 270° C., preferably between 180 and 250° C. A suitable pressure range for the reaction is from about 50 mbar to about 1200 mbar, preferably from about 600 mbar to ambient pressure. The lower applicable pressure is limited by loss of carboxylic acids from the reaction mixture by distillation.

The iodine value and the mean degree of polymerization can be determined as described above.

It is obvious that instead of the monocarboxylic acids b) and the dicarboxylic acids c) suitable derivatives of the carboxylic acids like their anhydrides, their halogenides, and their esters, preferably their esters with short chain alcohols like methanol or ethanol, may be used to obtain the polyglycerol esters contained in the cosmetic composition according to the invention.

Preferred polyglycerols used in the process for obtaining the polyglycerol partial ester contained in the cosmetic composition according to the present invention comprise an average degree of polymerization of 2.5 to 6, particularly preferably of 3 to 4.5.

Particularly preferred polyglycerols used in the process for obtaining the polyglycerol partial ester contained in the cosmetic composition according to the present invention are selected from the group consisting of polyglycerols with
when the degree of polymerization is in the range of 2.5-2.75, then the amount of diglycerol is larger than 40 wt. % and the amount of pentaglycerol and bigger oligomers is larger than 7 wt. %,
when the degree of polymerization is in the range 2.75-3.25, then the amount of diglycerol is larger than 35 wt. % and the amount of pentaglycerol and bigger oligomers is larger than 10 wt. %,
when the degree of polymerization is in the range of 3.25-3.75, then the amount of diglycerol is larger than 30 wt. % and the amount of pentaglycerol and bigger oligomers is larger than 15 wt. %,
when the degree of polymerization is in the range of 3.75-4.5, then the amount of diglycerol is larger than 25 wt. % and the amount of pentaglycerol and bigger oligomers is larger than 20 wt. % and
when the degree of polymerization is in the range of 4.5-6.0, then the amount of diglycerol is larger than 20 wt. % and the amount of pentaglycerol and bigger oligomers is larger than 30 wt. %,
whereby the wt. % refer to the total amount of polyglycerol.

The polyglycerol used in the esterification process described above can be produced by several methods. Suitable methods for the production of polyglycerol include polymerization of glycidol (e. g. with base catalysis), polymerization of epichlorohydrin (e. g. in the presence of equimolar amounts of a base like NaOH), or polycondensation of glycerol.

The preferred method for the purpose of this invention is condensation of glycerol, in particular in the presence of catalytic amounts of base, preferably NaOH or KOH. Suitable reaction conditions include temperatures of 220-260° C. and reduced pressure (20-800 mbar, preferably 50-500 mbar) to facilitate removal of reaction water from the mixture. The progress of the condensation reaction may be followed by measuring refractive index, viscosity, or hydroxyl value of the reaction product.

A particularly preferred method, which results in a desired broader polydispersity of the product, comprises the steps of
reacting glycerol in a condensation reaction in the presence of a catalytic amount (0.2-5% by weight) of base at a temperature from about 220-260° C. at a pressure between 250 and 1000 mbar while removing reaction water by distillation until the reaction mixture contains less than 70% (preferably less than 60%) of glycerol
continuing the condensation reaction at a lower pressure between 20 and 200 mbar while removing reaction water and glycerol by distillation until the hydroxyl value of the reaction mixture is lower than 1400 (preferably lower than 1200), and
optionally neutralizing the catalyst with an acid.

The iodine value and the polydispersity index can be determines as described above.

A preferred method for preparation of the polyglycerol partial esters contained in the cosmetic composition according to the invention makes use of the proviso that the ratio by weight of polyglycerol mixture to monocarboxylic acid is in the range from 0.11 to 1, preferably in the range from 0.11 to 0.67.

Preferred cosmetic compositions according to the invention contain the aforementioned polygylcerol partial esters in an amount from 0.1 wt. % to 10.0 wt. %, more preferably from 0.15 wt. % to 5.0 wt. %, even more preferred from 0.2 wt. % to 4.0 wt. % based on the total weight of the composition.

Preferred cosmetic compositions according to the invention are emulsions, preferably oil in water or water in oil emulsions or multiple emulsions in the form of lotions, creams, sprays or microemulsions.

The cosmetic composition according to the invention can, for example, comprise at least one additional component selected from the group of
emollients,
emulsifiers and surfactants,
thickeners/viscosity regulators/stabilizers,
UV photoprotective filters,
antioxidants and vitamins,
hydrotropes (or polyols),
solids and fillers,
film formers,
pearlescent additives,
deodorant and antiperspirant active ingredients,
insect repellents,
self-tanning agents,
preservatives,
conditioners,
perfumes,
dyes,
biogenic active ingredients,
care additives,
superfatting agents and
solvents.

Substances to be used as additional components are well known to the artesian, for further exemplary substances the list in for example DE 102008001788 can be consulted.

Preferred cosmetic compositions according to the invention contain at least one additional component selected from cationic surfactants and polymers containing at least one quarternary ammonium group. Preferred cationic surfactants are selected from quaternary ammonium salts containing organic carbon chains like for example cetrimonium chloride, behentrimonium chloride, dicetyldimonium chloride, quaternium-18, behentrimonium methosulfate, distearoylethyl dimonium chloride, palmitamidopropyltrimonium chloride, ricinoleamidopropyltrimonium methosulfate, distearyldimonium chloride and quaternium-87.

Preferred cosmetic compositions according to the invention therefore may contain
0 wt. % to 10 wt. %, preferably von 0.1 wt. % bis 7.5 wt. % of at least one emulsifier,
0 wt. % to 10 wt. %, preferably von 0.1 wt. % bis 7.5 wt. % of at least one consistency enhancer,
0.1 wt. % to 10 wt. %, preferably von 0.1 wt. % bis 7.5 wt. % of at least one cationic surfactant and/or at least one polymer containing at least one quarternary ammonium group
0 wt. % to 20 wt. %, preferably von 0.1 wt. % bis 17.5 wt. % of at least one cosmetic oil or emollient, wherein all percentages base on the total weight of the composition.

Preferably, the cosmetic compositions are cleaning and care compositions.

Cleaning and care compositions are understood as meaning primarily those compositions for the treatment of hair or skin, in particular hair. Such hair care compositions are, for example, hair shampoos, liquid soaps, hair rinses, permanent wave neutralizing lotions, hair colour shampoos, hair setting compositions, hair arranging compositions, hair styling preparations, blow-drying lotions, foam setting compositions, hair treatments, leave-in conditioners and other cleaning and care formulations.

Another part of the invention is the use of the above described polyglycerol partial esters contained in the cosmetic compositions according to the invention in cosmetic compositions, especially in hair care compositions, wherein polyglycerol partial esters contained in preferred cosmetic compositions according to the invention are particularly preferably used.

Another part of the invention is the use of the above described polyglycerol partial esters contained in the cosmetic compositions according to the invention as a conditioning agent for hair, wherein polyglycerol partial esters contained in preferred cosmetic compositions according to the invention are particularly preferably used.

Another part of the invention is the use of the above described polyglycerol partial esters contained in the cosmetic compositions according to the invention as a hair protecting agent, especially in protection from heat, wherein polyglycerol partial esters contained in preferred cosmetic compositions according to the invention are particularly preferably used.

Another part of the invention is the use of the above described polyglycerol partial esters contained in the cosmetic compositions according to the invention as a hair repair agent, especially in repairing thin and fine hair, wherein polyglycerol partial esters contained in preferred cosmetic compositions according to the invention are particularly preferably used.

Another part of the invention is the use of the above described polyglycerol partial esters contained in the cosmetic compositions according to the invention as a hair strengthening agent, especially in strengthening thin and fine hair, wherein polyglycerol partial esters contained in preferred cosmetic compositions according to the invention are particularly preferably used.

Yet another part of the invention is the use of the cosmetic compositions according to the invention in the areas described in each of the uses for the polyglycerol partial esters above, wherein preferred cosmetic compositions according to the invention are particularly preferably used.

EXAMPLES

Example 1

PGE 24

500 g glycerol and 2.5 g of potassium hydroxide were heated to 240° C. at a pressure of 400 mbar while sparging with nitrogen. Reaction water was continuously distilled from the reaction mixture. When the refractive index reached 1.4910 the reaction was stopped by cooling The product had a hydroxyl value of 1170 mg KOH/g, a polydispersity index of 1.33, and contained 5.5% of cyclic polyglycerols.

240 g of this product were reacted with 551.6 g of partially hydrogenated tallow fatty acid (C16/18) with an iodine value of 20 at a temperature of 240° C. while sparging with nitrogen. Reaction water was continuously distilled from the mixture. When the acid value reached <1 mg KOH/g, the reaction was stopped by cooling.
Hydroxyl value: 210 mg KOH/g
Acid value: 1.1 mg KOH/g
Saponification value: 153 mg KOH/g
HLB (calculated): 6.1

Example 2

PGE 25

500 g glycerol and 2.5 g of potassium hydroxide were heated to 240° C. at a pressure of 400 mbar while sparging with nitrogen. Reaction water was continuously distilled from the reaction mixture. When the refractive index reached 1.4840, the pressure was lowered to 50 mbar and the condensation reaction was continued for 1.5 h while glycerol was distilled from the product.

The product had a hydroxyl value of 1156 mg KOH/g, a polydispersity index of 1.17, and contained 5.2% of cyclic polyglycerols.

240 g of this product were reacted with 275.8 g of partially hydrogenated tallow fatty acid (C16/18) with an iodine value of 20 at a temperature of 240° C. while sparging with nitrogen. Reaction water was continuously distilled from the mixture. When the acid value reached <1 mg KOH/g, the reaction was stopped by cooling.
Hydroxyl value: 191 mg KOH/g
Acid value: 0.1 mg KOH/g
Saponification value: 156 mg KOH/g
HLB (calculated): 9.8

Example 3

PGE 17

500 g glycerol and 2.5 g of potassium hydroxide were heated to 240° C. at a pressure of 400 mbar while sparging with nitrogen. Reaction water was continuously distilled from the reaction mixture. When the refractive index reached 1.4840, the pressure was lowered to 50 mbar and the condensation reaction was continued for 1.5 h while glycerol was distilled from the product.

The product had a hydroxyl value of 1156 mg KOH/g, a polydispersity index of 1.17, and contained 5.2% of cyclic polyglycerols.

254.8 g of this product were reacted with 545.2 g of palmitic acid (C16) at a temperature of 240° C. while sparging with nitrogen. Reaction water was continuously distilled from the mixture. When the acid value reached <1 mg KOH/g, the reaction was stopped by cooling.
Hydroxyl value: 209 mg KOH/g
Acid value: 0.6 mg KOH/g
Saponification value: 160 mg KOH/g
HLB (calculated): 6.4

Example 4

PGE 18

500 g glycerol and 2.5 g of potassium hydroxide were heated to 240° C. at a pressure of 400 mbar while sparging with nitrogen. Reaction water was continuously distilled from the reaction mixture. When the refractive index reached 1.4840, the pressure was lowered to 50 mbar and the condensation reaction was continued for 1.5 h while glycerol was distilled from the product.

The product had a hydroxyl value of 1156 mg KOH/g, a polydispersity index of 1.17, and contained 5.2% of cyclic polyglycerols.

236.3 g of this product were reacted with 563.7 g of stearic acid (C18) at a temperature of 240° C. while sparging with nitrogen. Reaction water was continuously distilled from the mixture. When the acid value reached <1 mg KOH/g, the reaction was stopped by cooling.
Hydroxyl value: 194 mg KOH/g
Acid value: 0.6 mg KOH/g
Saponification value: 147 mg KOH/g
HLB (calculated): 5.9

Example Formulations

Hot processing was applied in all cases; all given amounts are wt.-%.

Hair Rinse Formulations

| Formulation Example # | 1 | 2 | 3 | 4 |
|---|---|---|---|---|
| TEGINACID ® C, Evonik Goldschmidt GmbH (INCI: Ceteareth-25) | 0.5 | 0.5 | 0.5 | 0.5 |
| TEGO ® Alkanol 16, Evonik Goldschmidt GmbH (INCI: Cetyl Alcohol)) | 4 | 4 | 4 | 4 |
| VARISOFT ® 300, 30%-ig, Evonik Goldschmidt GmbH (INCI: Cetrimonium Chloride) | 3.3 | | | |
| VARISOFT PATC, Evonik Goldschmidt (INCI: Palmitamidopropyltrimonium Chloride) | | 3.3 | | |
| VARISOFT EQ 65 Pellets, Evonik Goldschmidt (INCI: Distearoylethyl Dimonium Chloride) | | | 3.3 | |
| VARISOFT BT 85 Pellets, Evonik Goldschmidt (INCI: Behentrimonium Chloride) | | | | 3.3 |
| Demin. water | ad 100 | | | |
| Citric acid | ad. pH 4.0 ± 0.3 | | | |
| Example 1 | 0.5 | 0.5 | | |
| Example 2 | | | 0.5 | 0.5 |

Body Wash Formulations

| Formulation Example # | 5 | 6 | 7 | 8 |
|---|---|---|---|---|
| TEXAPON ® NSO, Cognis, 28%-ig (INCI: Sodium Laureth Sulfate) | 30 | 30 | 30 | 30 |
| TEGOSOFT ® PC 31, Evonik Goldschmidt GmbH (INCI: Polyglyceryl-3 Caprate) | 0.5 | 0.5 | 0.5 | 0.5 |
| Perfume | 0.3 | 0.3 | 0.3 | 0.3 |
| Water | 54.1 | 54.1 | 54.1 | 54.1 |
| TEGOCEL ® HPM 4000, Evonik Goldschmidt GmbH (INCI: Hydroxypropyl Methylcellulose) | 0.3 | 0.3 | 0.3 | 0.3 |
| REWOTERIC ® AM C, Evonik Goldschmidt GmbH, 32%-ig (INCI: Sodium Cocoamphoacetate) | 10 | 10 | 10 | 10 |
| Citric acid monohydrate | 0.5 | 0.5 | 0.5 | 0.5 |
| REWODERM ® LI S 80, Evonik Goldschmidt GmbH (INCI: PEG-200 Hydrogenated Glyceryl Palmate; PEG-7 Glyceryl Cocoate) | 2 | 2 | 2 | 2 |
| TEGO ® Pearl N 300, Evonik Goldschmidt GmbH (INCI: Glycol Distearate; Laureth-4; Cocamidopropyl Betaine) | 2 | 2 | 2 | 2 |
| Example 1 | 0.3 | | | |
| Example 2 | | 0.3 | | |
| Example 3 | | | 0.3 | |
| Example 4 | | | | 0.3 |

Mild Shower Bath

| Formulation Example # | 9 | 10 | 11 | 12 |
|---|---|---|---|---|
| TEXAPON ® NSO, Cognis, 28%-ig (INCI: Sodium Laureth Sulfate) | 27 | 27 | 27 | 27 |
| REWOPOL ® SB FA 30, Evonik Goldschmidt GmbH (INCI: Disodium Laureth Sulfosuccinate) | 12 | 12 | 12 | 12 |
| TEGOSOFT ® LSE 65 K SOFT, Evonik Goldschmidt GmbH (INCI: Sucrose Cocoate) | 2 | 2 | 2 | 2 |
| Water | 39 | 39 | 39 | 39 |
| REWOTERIC ® AM C, Evonik Goldschmidt GmbH, 32%-ig (INCI: Sodium Cocoamphoacetate) | 13 | 13 | 13 | 13 |
| Citric Acid (30% in water) | 3 | 3 | 3 | 3 |
| ANTIL ® 171 Evonik Goldschmidt GmbH (INCI: PEG-18 Glyceryl Oleate/Cocoate) | 1.5 | 1.5 | 1.5 | 1.5 |
| TEGO ® Pearl N 300 Evonik Goldschmidt GmbH (INCI: Glycol Distearate; Laureth-4; Cocamidopropyl Betaine) | 2 | 2 | 2 | 2 |
| Example 1 | 0.3 | | | |
| Example 2 | | 0.3 | | |
| Example 3 | | | 0.3 | |
| Example 4 | | | | 0.3 |

Body Wash Formulations

| Formulation Example # | 13 | 14 | 15 | 16 |
|---|---|---|---|---|
| Water | 93.75 | 93.75 | 93.95 | 93.95 |
| Propylene Glycol | 1 | 1 | 1 | 1 |
| Citric acid monohydrate | q.s. | q.s. | q.s. | q.s. |
| TEGO ® Alkanol 16, Evonik Goldschmidt GmbH (INCI: Cetyl alcohol) | 3 | 3 | 3 | 3 |
| VARISOFT ® PATC, Evonik Goldschmidt GmbH (INCI: Palmitamidopropyltrimonium Chloride) | 1.75 | 1.75 | 1.75 | 1.75 |
| Example 1 | 0.3 | | | |
| Example 2 | | 0.3 | | |
| Example 3 | | | 0.3 | |
| Example 4 | | | | 0.3 |
| Perfume, preservative | q.s. | q.s. | q.s. | q.s. |

Leave-in Conditioning Mousse

| Formulation Example # | 17 | 18 | 19 | 20 |
|---|---|---|---|---|
| Example 1 | 0.3 | | | |
| Example 2 | | 0.3 | | |
| Example 3 | | | 0.3 | |
| Example 4 | | | | 0.3 |
| ABIL ® B 88183, Evonik Goldschmidt GmbH (INCI: PEG/PPG-20/6 Dimethicone) | 0.4 | 0.4 | 0.4 | 0.4 |
| TAGAT ® CH-40 (INCI: PEG-40 Hydrogenated Castor Oil) | 0.5 | 0.5 | 0.5 | 0.5 |
| Perfume | 0.2 | 0.2 | 0.2 | 0.2 |
| TEGO ® Betain 810, Evonik Goldschmidt GmbH, 38%-ig (INCI: Capryl/Capramidopropyl Betaine) | 4.2 | 4.2 | 4.2 | 4.2 |
| Water | 93.5 | 93.5 | 93.5 | 93.5 |
| Panthenol | 0.2 | 0.2 | 0.2 | 0.2 |
| LACTIL ®, Evonik Goldschmidt GmbH (INCI: Sodium Lactate; Sodium PCA; Glycine; Fructose; Urea; Niacinamide; Inositol; Sodium benzoate; Lactic Acid) | 0.3 | 0.3 | 0.3 | 0.3 |
| Citric Acid (30% in water) | 0.4 | 0.4 | 0.4 | 0.4 |

Creamy Shaving Foam

| Formulation Example # | Phase | 21 | 22 | 23 |
|---|---|---|---|---|
| Water | A | 50 | 50 | 50 |
| Coconut Fatty Acid | A | 1.4 | 1.4 | 1.4 |
| Monoethanolamine | A | 1.3 | 1.3 | 1.3 |

| Formulation Example # | Phase | 21 | 22 | 23 |
|---|---|---|---|---|
| Myristic Acid | A | 3.5 | 3.5 | 3.5 |
| TEGOSOFT ® LSE 65 K Evonik Goldschmidt (INCI: Sucrose Cocoate) | B | 2 | 2 | 2 |
| Example 1 | B | 1.7 | | |
| Example 2 | B | | 1.7 | |
| Example 3 | B | | | 1.7 |
| TEGO ® Betain 810 Evonik Goldschmidt (INCI: Capryl/Capramidopropyl Betaine) | C | 7.6 | 7.6 | 7.6 |
| Glycerin | C | 5 | 5 | 5 |
| Perfume | C | 0.3 | 0.3 | 0.3 |
| Water | C | 26.5 | 26.5 | 26.5 |
| TEGOCEL ® HPM 50 Evonik Goldschmidt (INCI: Hydroxypropyl Methylcellulose) | C | 0.7 | 0.7 | 0.7 |

The invention claimed is:

1. A cosmetic composition containing a polyglycerol partial ester having the structure of Formula (I)

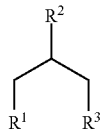

Formula (I)

wherein $R^1$, $R^2$ and $R^3$ independent from each other, equal or different, are selected from the group consisting of:
— OH,
— $OR^4$, wherein $R^4$ is a linear, unsubstituted acyl radical having a chain length of from 16 to 22 carbon atoms with the proviso that monocarboxylic acids obtained from the acyl radical by saponification have an iodine value of smaller than 50, and
— $OR^5$, wherein $R^5$ is a radical having the structure of Formula (I) wherein one of $R^1$, $R^2$ and $R^3$ has a direct bond to the oxygen of — $OR^5$
wherein each molecule of the polyglycerol partial ester comprises at least one of each — $OR^4$ and — $OR^5$, with the provisos that the polyglycerol obtained by hydrolysis or alcoholysis of the polyglycerol partial ester comprises an HLB value from 2 to 10, an average degree of polymerization of from 2 to 8 and the polydispersity index of said polyglycerol is greater than 0.75.

2. The cosmetic composition according to claim 1, wherein at least 1% of the polyglycerol obtained by hydrolysis or alcoholysis of the contained polyglycerol partial ester comprises cyclic structures.

3. The cosmetic composition according to claim 1, wherein the polyglycerol partial ester has a melting point of at least 25° C.

4. The cosmetic composition according to claim 1, wherein the polyglycerol partial ester is obtainable by a method comprising a process of esterification of
a) a polyglycerol mixture comprising an average degree of polymerization of from 2 to 8 with
b) at least one monocarboxylic acid comprising a carboxylic acid $HOR^4$, wherein $R^4$ is a linear, unsubstituted acyl radical with a chain length of from 16 to 22 carbon atoms with the proviso that the at least one carboxylic acid bears an iodine value of smaller than 50.

5. The cosmetic composition according to claim 1, wherein said composition is a hair care composition.

6. The cosmetic composition according to claim 5, wherein said composition is a conditioning agent for hair, a hair protecting agent, a hair repair agent or a hair strengthening agent.

7. The cosmetic composition according to claim 1, wherein said HLB value is from 2.5 to 8.

8. The cosmetic composition according to claim 1, wherein said HLB value is from 3 to 6.

* * * * *